United States Patent [19]

Abramson et al.

[11] Patent Number: 4,834,846

[45] Date of Patent: May 30, 1989

[54] PROCESS FOR DEBLOCKING N-SUBSTITUTED β-LACTAMS

[75] Inventors: Newton L. Abramson, Edison; Sandor Karady, Mountainside; Edward G. Corley, Old Bridge; Leonard M. Weinstock, Belle Mead, all of N.J.

[73] Assignee: Merck & Co., Inc., Rahway, N.J.

[21] Appl. No.: 129,496

[22] Filed: Dec. 7, 1987

[51] Int. Cl.$^4$ .................. C07D 205/04; C07D 403/04; C25B 3/02; C25B 3/04

[52] U.S. Cl. .................................... 204/59 R; 204/78; 204/74; 540/200; 540/362; 540/363; 540/364; 540/354; 540/357

[58] Field of Search .................. 204/59 R, 78, 74; 540/200, 362, 363, 364, 354, 357

[56] References Cited

PUBLICATIONS

G. Cainelli et al., "A Synthetic Approach to 4-Oxo and 4-Thioxo Azetidinones from Heterocumulenes and Ester Enolates . . . ", Tetrahedron Lett., 28, 3593–3596 (1987).

G. I. Georg et al., "Asymmetric Synthesis of (1′R,3R,4R)-4-Acetoxy-3-(1′-((tert-butyldimethyl-silyl)oxy)ethyl)-2-azetidinone . . . ," J. Am. Chem. Soc., 109, 1129–1135 (1987).

D. R. Kronenthal et al., "Oxidative N-Dearylation of 2-Azetidinones. p-Anisidine as a Source of Azetidinone Nitrogen," J. Org. Chem., 47, 2765–2768 (1982).

M. Masui et al., "Anodic Oxidation of Amides and Lactams Using N-Hydroxyphthalimide as a Mediator," Chem. Pharm. Bull., 34, 975–979 (1986).

M. Mori & Y. Ban, "Debenzylation of N-Benzyl-β-Lactams by Use of Anodic Oxidation," Heterocycles, 23, 317–323 (1985).

N. Okita et al., "Anodic Oxidation of N-Alkyl-β-Lactams," Heterocycles, 23, 247–250 (1985).

C-P. Chen et al., "Synthetically and Biologically Interesting N-Acylquinone Imine Ketals and N-Acylquinol Imine Ethers from Anodic Oxidation of Anilides," J. Am. Chem. Soc., 109, 946–948 (1987).

H. Ohmori et al., "Anodic Oxidation of Carboxamides. Part 3. The Mechanism of Anodic Cyclization of N-Methylcarbanilides," J. Chem. Soc., Perkin Trans. II, 1599–1605 (1981).

Tetrahedron Letters, vol. 29 No. 13, pp. 1497–1500, 1988; E. G. Corley et al.

Weinreb et al., J. Org. Chem., 40, 1356–1358 (1975).

*Primary Examiner*—John M. Ford
*Attorney, Agent, or Firm*—Raymond M. Speer; Hesna J. Pfeiffer

[57] ABSTRACT

This invention relates to a process for preparing β-lactams by electrochemically deblocking N-substituting β-lactams using anodic oxidation.

3 Claims, No Drawings

PROCESS FOR DEBLOCKING N-SUBSTITUTED β-LACTAMS

BACKGROUND OF THE INVENTION

This invention relates to a process for preparing β-lactams by electrochemically deblocking N-substituted β-lactams using anodic oxidation.

Formation of the azetidinone ring is a key step in the chemical synthesis of various β-lactam antibiotics. One synthetic strategy uses p-anisidine as the source of the ring nitrogen atom. Once the azetidinone ring is formed, the p-methoxyphenyl moiety can be removed by oxidative cleavage using oxidizing agents such as ceric ammonium nitrate. For example, G. Cainelli et al., *Tetrahedron Lett.*, 28, 3593–3596 (1987); G. I. Georg et al., *J. Am. Chem. Soc.*, 109, 1129–1135 (1987); and D. R. Kronenthal et al., *J. Org. Chem.*, 47, 2765–2768 (1982). Although frequently producing high yields of deblocked β-lactams, oxidation with ceric ammonium nitrate requires two (and works best with three) equivalents for each mole of substrate. Since ceric ammonium nitrate has a high molecular weight (548), a large-scale reaction requires massive quantities of reagent and generates large quantities of a heavy metal waste material. Furthermore, attempted use of catalytic amounts of ceric ammonium nitrate with a secondary oxidant has been reported to give inferior results. D. R. Kronenthal et al., *J. Org. Chem.*, 47, 2765–2768 (1982). The present invention provides a method of deblocking N-substituted β-lactams in good yields without the economic and environmental disadvantages inherent in traditional chemical oxidation methods.

Electrochemical deblocking of N-alkyl and N-benzyl lactams has been reported. For example, M. Masui et al., *Chem. Pharm. Bull.*, 34, 975–979 (1986); M. Mori and Y. Ban, *Heterocycles*, 23, 317–323 (1985); and M. Okita et al., *Heterocycles*, 23, 247–250 (1985). The cited references, however, do not disclose or suggest deblocking β-lactams in which a phenyl or substituted phenyl group is attached directly to the lactam ring nitrogen atom.

SUMMARY OF THE INVENTION

The present invention relates to an advantageous process for preparing β-lactams of Formula I

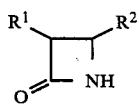

wherein
$R^1$ is:
(a) hydrogen;
(b) $C_1$–$C_6$ alkyl;
(c) $C_1$–$C_4$ alkyl substituted at the 1-position with a substituent selected from the group consisting of hydroxy, tris($C_1$–$C_4$ alkyl)silyloxy, and allyloxycarbonyloxy;
(d) $C_1$–$C_4$ fluorinated alkyl;
(e) azide; or
(f)

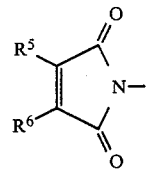

wherein $R^5$ and $R^6$ are independently hydrogen or $C_1$–$C_6$ alkyl, or $R^5$ and $R^6$ taken together are —CH=CH—CH=CH—; and $R^2$ is:
(a) hydrogen;
(b) $C_1$–$C_6$ alkyl or $C_1$–$C_6$ alkyl substituted with one or more substituents selected from the group consisting of phenyl and naphthyl;
(c) $C_2$–$C_6$ alkenyl or $C_2$–$C_6$ alkenyl substituted with one or more substituents selected from the group consisting of phenyl and naphthyl;
(d) phenyl or phenyl substituted with one or more substituents selected from the group consisting of $C_1$–$C_6$ alkyl, $C_2$–$C_6$ alkanoyl, $C_2$–$C_6$ alkoxycarbonyl, and halogen;
(e) $C_2$–$C_6$ alkanoyl;
(f) $C_2$–$C_6$ alkoxycarbonyl;
(g) benzoyl; or
(h) naphthoyl.

In particular, applicants have discovered a novel process for preparing deblocked β-lactams of Formula I comprising anodic oxidation of N-substituted β-lactams of Formula II

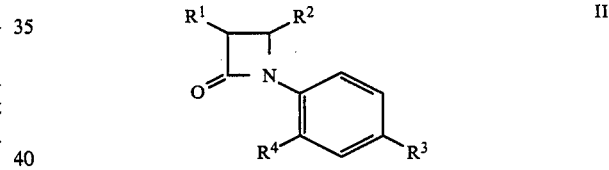

wherein
$R^1$ and $R^2$ are defined as above;
$R^3$ is $C_1$–$C_6$ alkoxy; and
$R^4$ is hydrogen or $C_1$–$C_6$ alkoxy;
wherein the anodic oxidation includes the steps of:
(a) providing a solution of the N-substituted β-lactam and a supporting electrolyte in a suitable solvent;
(b) immersing a substantially inert anode and a suitable cathode in the solution;
(c) passing a direct current at a potential of from about 1.2 volts to about 2.5 volts through the solution; and
(d) isolating the deblocked β-lactam.

The term "$C_1$–$C_6$ alkyl" refers to straight or branched chain aliphatic hydrocarbons having from 1 to 6 carbon atoms and is also referred to as lower alkyl. Examples of $C_1$–$C_6$ alkyl are methyl, ethyl, propyl, butyl, pentyl, hexyl, and the isomeric forms thereof.

Substitution at the 1-position of $C_1$–$C_4$ alkyl refers to $C_1$–$C_4$ alkyl bearing a substituent on the carbon atom most proximately attached to the β-lactam ring. For example, 1-hydroxy substituted $C_1$–$C_4$ includes hydroxymethyl, 1-hydroxyethyl, 1-hydroxypropyl, 1-hydroxybutyl, 1-hydroxy-2-methylpropyl, and their optical isomer forms. Similar substitution is possible for tris($C_1$–$C_4$ alkyl)-silyloxy and allyloxycarbonyloxy groups. For example, 1-tris($C_1$–$C_4$ alkyl)silyloxy-substituted $C_1$–$C_4$ alkyl includes (trimethylsilyloxy)methyl, 1-(trimethylsilyloxy)ethyl, (t-butyldimethylsilyloxy)methyl, 1-(t-butyldimethylsilyloxy)ethyl, and the like.

The term "$C_1$–$C_4$ fluorinated alkyl" refers to straight or branched chain alkyl groups having from 1 to 4 carbon atoms in which one or more hydrogen atoms are replaced with fluorine atoms. Examples of $C_1$–$C_4$ fluorinated alkyl are fluoromethyl, difluoromethyl, trifluoromethyl, 1-and 2-fluoroethyl, 1,1-difluoroethyl, 2,2,2-trifluoroethyl, perfluoroethyl; other similarly monofluorinated, polyfluorinated, and perfluorinated ethyl, propyl, and butyl groups; and the isomeric forms thereof.

The term "$C_2$–$C_6$ alkenyl" refers to straight or branched chain hydrocarbon groups having from 2 to 6 carbon atoms and possessing one carbon-carbon double bond. Examples of $C_2$–$C_6$ alkenyl are vinyl; allyl; 2-and 3-butenyl; 2-, 3-, and 4-pentenyl; 2-, 3-, 4-, and 5-hexenyl; and the isomeric forms thereof.

The term "$C_2$–$C_6$ alkanoyl" refers to straight or branched chain alkanoyl groups having from 2 to 6 carbon atoms. Examples of $C_2$–$C_6$ alkyl are acetyl, propanoyl, butanoyl, pentanoyl, hexanoyl, and the isomeric forms thereof.

The term "$C_2$–$C_6$ alkoxycarbonyl" refers to straight or branched chain alkoxycarbonyl groups having from 2 to 6 carbon atoms. Examples of $C_1$–$C_6$ alkoxy are methoxycarbonyl, ethoxycarbonyl, propoxycarbonyl, butoxycarbonyl, pentyloxycarbonyl, hexloxycarbonyl, and the isomeric forms thereof.

The term "naphthoyl" refers to 1-and 2-naphthalenecarbonyl groups.

The term "$C_1$–$C_6$ alkoxy" refers to straight or branched chain alkyl oxy groups having from 1 to 6 carbon atoms. Examples of $C_1$–$C_6$ alkoxy are methoxy, ethoxy, propoxy, butoxy, pentyloxy, hexyloxy, and the isomeric forms thereof.

Example of halogen are fluorine, chlorine, bromine, and iodine.

When at least one substituent $R^1$ or $R^2$ is a group other than hydrogen, the position at which it is attached is asymmetric and the compounds of Formulas I and II are racemic. One skilled in the art would understand that compounds of Formula I or their precursors could be resolved into enantiomeric and diasteriomeric components. It is understood that this invention encompasses electrochemical deprotection of the racemic mixtures and the enantiomers.

DESCRIPTION OF THE INVENTION

The process of this invention may be effectuated using the general anodic oxidation procedure illustrated in the following Scheme A. Unless otherwise specified, the various substituents are defined as above for Formulas I and II.

SCHEME A

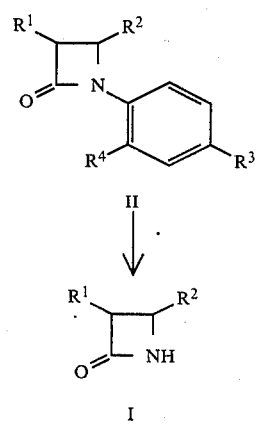

The N-substituted β-lactams of Formula II can be prepared using methods known in the art. For example, G. Caineelli et al. *Tetrahedron Lett.*, 28, 3593–3596 (1987); G. I. Georg et al., *J. Am. Chem. Soc.*, 109, 1129–1135 (1987); and D. R. Kronenthal et al., *J. Org. Chem.*, 47, 2765–2768 (1982). Anodic oxidation of N-substituted β-lactams of Formula II is accomplished by passing a direct current at a suitable potential through a solution of the N-substituted β-lactam in a suitable solvent containing a supporting electrolyte. A suitable potential is a potential sufficiently great to induce electrolysis of the N-protecting group but not so large as to cause over-oxidation and other undesirable side reactions. Voltamograms of compounds of Formula II indicate two waves in aqueous acetonitrile at about 1.2–1.4 volts and about 1.5–1.6 volts. By analogy to anodic oxidation of p-methoxyanilides, these waves correspond to one-and two-electron oxidations, respectively. See C. -P. Chen et al., *J. Am. Chem. Soc.*, 109, 946–948 (1987); and H. Ohmori et al., *J. Chem. Soc. Perkin Trans.* II, 1599–1605 (1981). Electrolyses at potentials corresponding to the first wave (1.2–1.4 volts) produced lower yields and greater quantities of by-products than electrolyses at potentials corresponding to the second wave (1.5–1.6 volts). Electrolyses can be performed at potentials up to about 2.5 volts, where side reactions involving reactants and solvent interfere with yields and purity. Preferred electrode potentials lie in the range of 1.5–2.0 volts.

An electric current is passed through the solution using suitable electrodes, which are prepared using substantially inert anode materials and suitable cathode materials. A suitable substantially inert anode material is an electrically conducting substance that can remove electrons from components of the reaction medium, including compounds of Formula II, but which does not itself form significant quantities of by-products by self-ionization or by otherwise chemically reacting with reagents, intermediates, or reaction products. Example of suitable anode materials include noble metals, such as palladium and platinum, and various forms of elemental carbon, such as graphite, carbon felt, and vitreous carbon. A preferred anode material is vitreous carbon. A suitable cathode is an electrically conducting substance that can act as an electron source, but which does not itself form significant quantities of by-products by self-ionization or by otherwise chemically reacting with reagents, intermediates, or reaction products. Cathodes used in the process of this invention can be made from a greater variety of materials than the anode. For example, use of stainless steel instead of platinum has essentially no effect on the yields or purity of compounds of Formula I. A preferred cathode material is platinum.

Electrolyses can also be performed under constant current conditions. For example, on the scale used in the following illustrative examples, a current of 50 to 500 μA readily removes the p-methoxyphenyl protecting group. On a larger scale, a correspondingly higher current would be appropriate.

Suitable solvents for deblocking N-substituted β-lactams of Formula II by anodic oxidation are liquids in which the various reactants can be dissolved or suspended but which are otherwise chemically inert. Suitable solvents include water, suitable water-miscible organic solvents, or mixtures thereof. The particular solvent or solvent mixture and the amount of the solvent or solvent mixture used are determined by the specific quantities and proportions of N-substituted β-lactam, supporting electrolyte, and electric current. Suitable water-miscible organic solvents are organic liquids that are resistant to anodic oxidation under the conditions used. Examples of suitable water-miscible organic solvents include alkanols, such as methanol and ethanol; alkanoic acids, such as acetic acid and propanoic acid; alkanones, such as acetone and methyl ethyl ketone; cycanoalkanes, such as acetonitrile and propanenitrile; and other such solvents known in the art. A preferred solvent is aqueous acetonitrile, preferably one part (by volume) of water to ten parts acetonitrile.

A suitable supporting electrolyte is a chemical substance, preferably an ionizable salt, that promotes the electrolysis by increasing the electrical conductivity of the reaction medium but which does not itself form significant quantities of by-products by reacting with reagents, intermediates, or reaction products. The amount of supporting electrolyte used depends upon the particular quantities and porportions of electric current, solvent, specific supporting electrolyte, and N-substituted β-lactam used. In general, a preferred amount of electrolyte is about 1-5% (by weight) in an aqueous solvent mixture. Examples of suitable supporting electrolytes include alkali metal perchlorates, such as lithium perchlorate and sodium perchlorate; ammonium and tetraalkylammonium salts, such as ammonium or trimethylammonium perchlorate, sulfate, tetrafluoroborate, methanesulfonate, and trifluoromethanesulfonate; and other supporting electrolytes known in the art. The reaction medium can be slightly acidic or basic with little effect on yields and purity, but slight acidification with a weak acid such as acetic acid inhibits formation of a tarry substance that occasionally forms at the cathode. A preferred supporting electrolyte is lithium perchlorate (preferably about 1% by weight).

Upon completion of the anodic oxidation, the deblocked β-lactams of Formula I are isolated from the reaction mixture and purified using methods known to those skilled in the art, such as solvent-solvent extraction, crystallization, and chromatography.

A preferred embodiment of this invention includes a process for preparing β-lactams of the following general formula

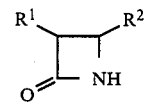

III wherein
R$^1$ is:
 (a) C$_1$–C$_6$ alkyl;
 (b) 1-[tris(C$_1$–C$_4$ alkyl)silyloxy]ethyl;
 (c) azide; or
 (d)

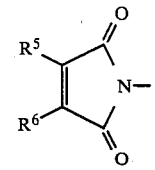

wherein R$^5$ and R$^6$ are both hydrogen, or R$^5$ and R$^6$ taken together are —CH=CH—CH=CH—; and
R$^2$ is:
 (a) C$_2$–C$_6$ alkenyl or C$_2$–C$_6$ alkenyl substituted with phenyl;
 (b) phenyl;
 (c) C$_2$–C$_6$ alkoxycarbonyl; or
 (d) benzoyl;
comprising anodic oxidation of N-substituted β-lactams of the following general formula

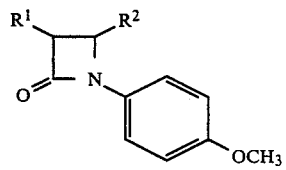

IV wherein R$^1$ and R$^2$ are defined as above;
wherein the anodic oxidation includes the steps of:
 (a) providing a solution of the N-substituted β-lactam and about 1% by weight of lithium perchlorate in aqueous acetonitrile;
 (b) immersing a carbon anode and a suitable cathode in the solution;
 (c) passing a direct current at a potential of from about 1.5 volts to about 2.0 volts through the solution; and
 (d) isolating the deblocked β-lactam.

The following examples further illustrate details for carrying out the process of this invention. The invention, which is set forth in the foregoing disclosure, is not to be construed or limited either in spirit or in scope by these examples. Those skilled in the art will readily understand that known variations in the following preparative procedures can be used to prepare these compounds. All temperatures are degrees Celsius unless otherwise noted.

Description Of The Preferred Embodiments

EXAMPLE 1

[3S-[3α(S*),4α]]-4-Benzoyl-3-[1-[[[(1,1-dimethyl-ethyl)-dimethyl]silyl]oxy]ethyl]-2-azetidinone

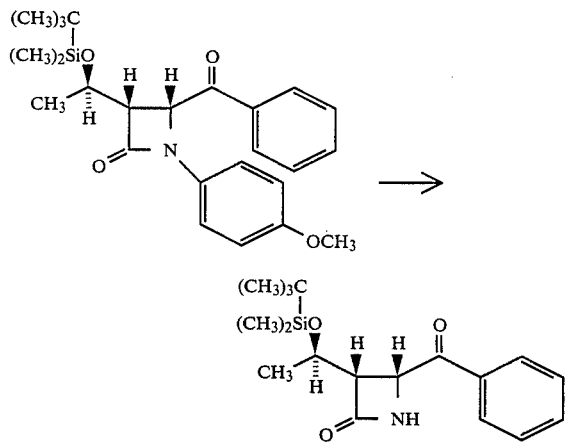

To a mixture of 90 ml of acetonitrile and 9 ml of water containing 0.99 g (9.3 mole) of lithium perchlorate was added 5.0 g (11.4 mmole) of [3S-[3α-(S*), 4α]]-4-benzoyl-3-[1-[[[(1,1-dimethylethyl)-dimethyl]silyl]oxy]ethyl-1-(4-methoxyphenyl)-2-azetidinone. A vitreous carbon anode and a platinum foil cathode were connected to a potentiostat (a stable source of direct current) and immersed in an undivided electrolysis cell containing the solution; a Ag/AgCl pH electrode was used as reference electrode. The solution was electroyzed at a constant potential of about 1.5 volts until the current dropped to near background levels and the starting material was consumed. Solvent was removed in vacuo. The resultant residue was dissolved in ethyl acetate, washed with 10% aqueous sodium sulfite, and again concentrated. The residue was purified by column chromatography on silica gel using 2:1 (by volume) hexane/ethyl acetate as eluent, affording the title compound as an oil (80% yield). Structure assignment was supported by nmr spectroscopy.

$^1$H nmr (CDCl$_3$) δ(ppm) −0.3 (s, 3H); −0.2 (s, 3H); 0.7 (s, 9H); 1.1 (d, 1H); 3.7 (t, 1H); 4.1 (m, 1H); 5.2 (d, 1H); 6.3 (s, 1H); 7.5 (m, 2H); 7.6 (m. 1H); 7.9 (m, 2H).

EXAMPLE 2

Preparation of β-Lactams in an Undivided Cell

The deblocked β-lactams listed in Table I were prepared from the corresponding N-substituted β-lactams by the method described in Example 1. After the extraction step, the compounds were isolated and purified by direct crystallization or by column chromatography.

TABLE I

| Example | R$^1$ | R$^2$ | R$^1$—R$^2$ Configuration | Yield |
|---|---|---|---|---|
| 2 | (CH$_3$)$_3$C—(CH$_3$)$_2$SiO—CH(CH$_3$)— | —C(O)C$_6$H$_5$ | trans | 80% |
|  | [3S—[3α(S*),4β]]-4-benzoyl-3-[1-[[[(1,1-dimethylethyl)dimethyl]silyl]oxy]ethyl]-2-azetidinone | | | |
| 3 | (CH$_3$)$_3$C—(CH$_3$)$_2$SiO—CH(CH$_3$)— | —CH=CH—C$_6$H$_5$ | trans | 95% |
|  | [3S—[3α(S*),4β(E)]]-3-[1-[[[(1,1-dimethylethyl)dimethyl]silyl]oxy]ethyl]-4-(2-phenylethenyl)-2-azetidinone | | | |
| 4 | ((CH$_3$)$_2$CH)$_3$SiO—CH(CH$_3$)— | ''''COOCH$_2$CH$_3$ | cis | 60% |
|  | [2R—[2α,3α(R*)]]-4-oxo-3-[1-[[tris(1-methylethyl)silyl]oxy]ethyl]-2-azetidinecarboxylic acid ethyl ester | | | |
| 5 | phthalimido | ''''C$_6$H$_5$ | (±)cis | 60% |
|  | cis-(±)-2-(2-oxo-4-phenyl-3-azetidinyl)-1H—isoindole-1,3(2H)—dione | | | |

TABLE I-continued

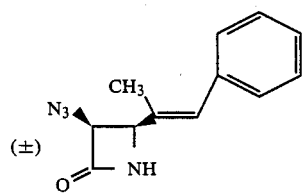

| Example | R¹ | R² | R¹—R² Configuration | Yield |
|---------|-----|-----|---------------------|-------|
| 6 | $CH_3$— | 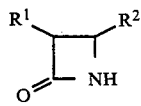 | (±)cis | 85% | cis-(±)-4-benzoyl-3-methyl-2-azetidinone

EXAMPLE 7 cis-(±)-3-Azido-4-benzoyl-2-azetidinone

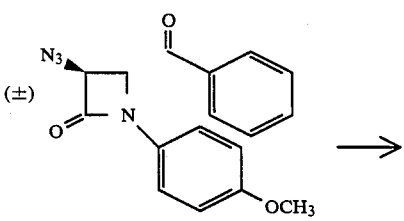

The title compound was prepared in 66% yield from the corresponding 1-(4-methoxyphenyl)-2-azetidinone by the method described in Example 1, except that oxidation was performed at 1.60 volts using a divided cell. The divided cell was constructed by inserting the cathode into a glass tube having a fritted glass filter at the end immersed in the solution.

EXAMPLE 8

[3α,4α(E)]-(±)-3-Azido-4-(1-methyl-2-phenylethenyl)-2-azetidinone

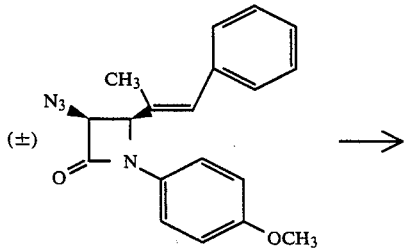

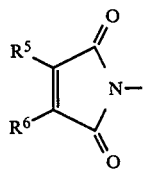

The title compound was prepared in 59% yield from the corresponding 1-(4-methoxyphenyl)-2-azetidinone by the divided-cell method described in Example 7, except that oxidation was performed at 1.45 volts.

What Is Claimed Is:

1. A process for preparing a compound having the formula

wherein
$R^1$ is:
(a) hydrogen;
(b) $C_1$-$C_6$ alkyl;
(c) $C_1$-$C_4$ alkyl substituted at the 1-position with a substituent selected from the group consisting of hydroxy, tris($C_1$-$C_4$ alkyl)silyloxy, and allyloxycarbonyloxy;
(d) $C_1$-$C_4$ fluorinated alkyl;
(e) azide: or
(f)

[structure with $R^5$, $R^6$, N]

wherein $R^5$ and $R^6$ are independently hydrogen or $C_1$-$C_6$ alkyl, or $R^5$ and $R^6$ taken together are —CH=CH—CH=CH—; and
$R^2$ is:
(a) hydrogen;

(b) C$_1$–C$_6$ alkyl or C$_1$–C$_6$ alkyl substituted with one or more substituents selected from the group consisting of phenyl and naphthyl;
(c) C$_2$–C$_6$ alkenyl or C$_2$–C$_6$ alkenyl substituted with one or more substituents selected from the group consisting of phenyl and naphthyl;
(d) phenyl or phenyl substituted with one or more substituents selected from the group consisting of C$_1$–C$_6$ alkyl, C$_2$–C$_6$ alkanoyl, C$_2$–C$_6$ alkoxycarbonyl, and halogen;
(e) C$_2$–C$_6$ alkanoyl;
(f) C$_2$–C$_6$ alkoxycarbonyl;
(g) benzoyl; or
(h) naphthoyl;

comprising anodic oxidation of a N-substituted β-lactam of the formula

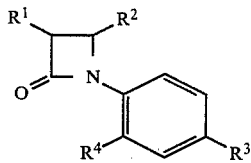

wherein
R$^1$ and R$^2$ are defined as above;
R$^3$ is C$_1$–C$_6$ alkoxy; and
R$^4$ is hydrogen or C$_1$–C$_6$ alkoxy;
wherein the anodic oxidation includes the steps of:
(a) providing a solution of the N-substituted β-lactam and a supporting electrolyte in a suitable solvent;
(b) immersing a substantially inert anode and a suitable cathode in the solution;
(c) passing a direct current at a potential of from about 1.2 volts to about 2.5 volts through the solution; and
(d) isolating the deblocked β-lactam.

2. A process according to claim 1 for preparing a compound of the formula

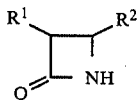

wherein
R$^1$ is:
(a) C$_1$–C$_6$ alkyl;
(b) 1-[tris(C$_1$–C$_4$ alkyl)silyloxy]ethyl;
(c) azide; or
(d)

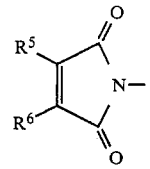

wherein R$^5$ and R$^6$ are both hydrogen, or R$^5$ and R$^6$ taken together are —CH=CH—CH=CH—; and
R$^2$ is:
(a) C$_2$–C$_6$ alkenyl or C$_2$–C$_6$ alkenyl substituted with phenyl;
(b) phenyl;
(c) C$_2$–C$_6$ alkoxycarbonyl; or
(g) benzoyl;

comprising anodic oxidation of a N-substituted β-lactam of the formula

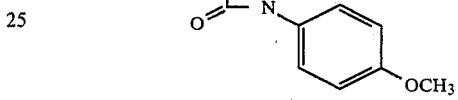

wherein R$^1$ and R$^2$ are defined as above;
wherein the anodic oxication includes the steps of:
(a) providing a solution of the N-substituted β-lactam and about 1% by weight of lithium perchlorate in aqueous acetonitrile;
(b) immersing a carbon anode and a suitable cathode in the solution;
(c) passing a direct current at a potential of from about 1.5 volts to about 2.0 volts through the solution; and
(d) isolating the deblocked β-lactam.

3. A process according to claim 2 for preparing a compound selected from the group consisting of:
[3S-[3α(S*),4α]]-4-benzoyl-3-[1-[[[(1,1-dimethyl-ethyl)-dimethyl]silyl]oxy]ethyl]-2-azetidinone,
[3S-[3α(S*),4β]]-4-benzoyl-3-[1-[[[(1,1-dimethyl-ethyl)-dimethyl]silyl]oxy]ethyl]-2-azetidinone,
[3S-[3α(S*),4β(E)]]-3-[1-[[[(1,1-dimethylethyl)dimethyl]silyl]oxy]ethyl]-4-(2-phenylethenyl)-2-azetidinone,
[2R-[2α,3α(R*)]]-4-oxo-3-[1-[[tris(1-methylethyl)-silyl]oxy]ethyl]-2-azetidinecarboxylic acid ethyl ester,
cis-(±)-2-(2-oxo-4-phenyl-3-azetidinyl)-1H-isoindole-1,3(2H)-dione,
cis-(±)-4-benzoyl-3-methyl-2-azetidinone,
cis-(±)-3-azido-4-benzoyl-2-azetidinone, and
[3α,4α(E)]-(±)-3-azido-4-(1-methyl-2-phenyl-ethenyl)-2-azetidinone.

* * * * *